(12) United States Patent
Shutov et al.

(10) Patent No.: US 9,139,506 B2
(45) Date of Patent: Sep. 22, 2015

(54) PROCESS FOR MAKING HYBRID POLYESTER-POLYETHER POLYOLS

(71) Applicants: Pavel L. Shutov, Terneuzen (NL); David S. Laitar, Midland, MI (US); David A. Babb, Lake Jackson, TX (US)

(72) Inventors: Pavel L. Shutov, Terneuzen (NL); David S. Laitar, Midland, MI (US); David A. Babb, Lake Jackson, TX (US)

(73) Assignee: Dow Global Technologies LLC, Midland, MI (US)

( * ) Notice: Subject to any disclaimer, the term of this patent is extended or adjusted under 35 U.S.C. 154(b) by 0 days.

(21) Appl. No.: 14/365,961

(22) PCT Filed: Dec. 10, 2012

(86) PCT No.: PCT/US2012/068834
§ 371 (c)(1),
(2) Date: Jun. 16, 2014

(87) PCT Pub. No.: WO2013/095976
PCT Pub. Date: Jun. 27, 2013

(65) Prior Publication Data
US 2014/0357887 A1 Dec. 4, 2014

Related U.S. Application Data

(60) Provisional application No. 61/577,073, filed on Dec. 18, 2011.

(51) Int. Cl.
| | | |
|---|---|---|
| C08G 64/00 | (2006.01) |
| C07C 67/465 | (2006.01) |
| C08G 65/00 | (2006.01) |
| C08G 65/26 | (2006.01) |
| C08G 63/02 | (2006.01) |

(52) U.S. Cl.
CPC .............. *C07C 67/465* (2013.01); *C08G 65/00* (2013.01); *C08G 65/2615* (2013.01); *C08G 65/2663* (2013.01)

(58) Field of Classification Search
CPC .............................. C08G 63/78; C08G 63/183
USPC .................................................. 528/271, 272
See application file for complete search history.

(56) References Cited

U.S. PATENT DOCUMENTS

| | | |
|---|---|---|
| 6,753,402 B1 | 6/2004 | Bauer |
| 2013/0289236 A1 | 10/2013 | Laitar |

FOREIGN PATENT DOCUMENTS

| | | |
|---|---|---|
| CA | 2790038 A | 8/2011 |
| DE | 19949091 A | 4/2001 |
| DE | 10201008410 A | 8/2011 |
| EP | 0090445 A | 5/1983 |
| WO | 2011-137011 A | 11/2011 |
| WO | 2012-022048 A | 2/2012 |
| WO | 2012/091968 A | 7/2012 |

*Primary Examiner* — Terressa Boykin
(74) *Attorney, Agent, or Firm* — Gary C Cohn PLLC

(57) ABSTRACT

Hybrid polyester-polyether polyols are prepared by polymerizing an alkylene oxide in the presence of a carboxylate initiator. The polymerization is catalyzed with a mixture of double metal cyanide catalyst complex and certain magnesium, group 3-group 15 metal or lanthanide series metal compounds. The presence of the magnesium, Group 3-Group 15 metal or lanthanide series metal (MG3-15LA) compound makes for consistently rapid activation of the double metal cyanide catalyst complex, even in the presence of carboxylate initiator compounds. This leads to greater productivity and reduced manufacturing costs due to shorter cycle times and less waste of raw materials due to the failure of the catalyst to become activated. Once the catalyst is activated, it often polymerizes the alkylene oxide at a faster rate that the DMC catalyst by itself.

8 Claims, No Drawings

PROCESS FOR MAKING HYBRID POLYESTER-POLYETHER POLYOLS

The invention relates to processes for preparing hybrid polyester-polyether polyols from carboxyl group-containing compounds and epoxides.

Hybrid polyester-polyether polyols are potentially useful raw materials for the manufacture of polyurethanes. They can be prepared by reacting a carboxylic acid compound, or a derivative thereof such as an anhydride, half-ester or amide, with a polymerizable oxirane and optionally a polyol. The oxirane polymerizes during the reaction to form polyether groups. The polymerization of the oxirane requires a catalyst. Among the catalysts that have been described for this polymerization include double metal cyanide (DMC) catalyst complexes, metal "superacid" salts, and certain tertiary amines. See, e.g., WO 2011/137011.

The use of a DMC catalyst complex potentially has certain advantages in making these hybrid polyester-polyether polyols. These advantages include fast polymerizations, the production of polyols that have low amounts of terminal unsaturation, and the ability to leave the catalyst residues in the product and, in doing so, avoiding expenses involved with catalyst removal.

DMC catalysts need to become "activated" before they become effective polymerization catalysts. This is normally done by exposing the DMC catalyst to a small amount of alkylene oxide at polymerization temperatures. A stage of the reaction known as the catalyst induction period then ensues. During this stage of the reaction, the DMC catalyst is believed to become converted in situ from an inactive form into a highly active form that rapidly polymerizes an alkylene oxide as long as it remains active. This catalyst induction period is typically an indeterminate period of time following the first introduction of alkylene oxide to the reactor. Very little or no polymerization occurs until the catalyst has become activated, so long activation times have a direct negative impact on the productivity of the process. It has proven to be especially difficult to activate the DMC catalyst in the hybrid polyester-polyether polyol-forming processes. The catalyst often does not become activated at all. Such a failure of the catalyst to activate typically will result in the abandonment of the attempt, and the process is started over again from the beginning. The reduction or elimination of the induction period at the start of the alkoxylation reaction is therefore seen to be highly desirable.

This invention is in one aspect a method for producing a hybrid polyester-polyether, comprising polymerizing at least one alkylene oxide in the presence of (1) a carboxylate initiator compound, (2) a double metal cyanide catalyst complex and (3) a magnesium, Group 3-Group 15 metal or lanthanide series metal compound in which a magnesium, Group 3-Group 15 metal or lanthanide series metal is bonded to at least one alkoxide, aryloxy, carboxylate, acyl, pyrophosphate, phosphate, thiophosphate, dithiophosphate, phosphate ester, thiophosphate ester, amide, siloxide, hydride, carbamate or hydrocarbon anion, and wherein the magnesium, Group 3-Group 15 metal or lanthanide series metal compound is devoid of halide anions.

The presence of the magnesium, Group 3-Group 15 metal or lanthanide series metal (MG3-15LA) compound makes for consistently rapid activation of the double metal cyanide catalyst complex, even in the presence of carboxylate initiator compounds. This leads to greater productivity and reduced manufacturing costs due to shorter cycle times and less waste of raw materials due to the failure of the catalyst to become activated. Once the catalyst is activated, it often polymerizes the alkylene oxide at a faster rate that the DMC catalyst by itself.

For purposes of this invention, the carboxylate initiator is a compound having at least one carboxyl (—COOH) or carboxylate (—COO$^-$) group, or a carboxylate precursor group which produces a carboxyl or carboxylate group under the conditions of the polymerization. The carboxylate initiator may contain one carboxyl or carboxylate precursor group, or any greater amount thereof. In preferred cases, the carboxylate initiator contains from one to 8, more preferably from one to six, still more preferably from one to four and even more preferably from 1 to 3 carboxyl groups or carboxylate precursor groups. The carboxylate initiator may contain various other groups, such as ester, amide, urethane, urea, ether, hydroxyl, primary amino, secondary amino, tertiary amino and the like.

Among the suitable carboxylate initiators include alkanoic monoacids having from 1 to 30 carbon atoms.

Other suitable carboxylate initiators include keto acids such as acetoacetic acid and pyruvic acid.

Other suitable carboxylate initiators include aromatic mono- and di-acids such as benzoic, mandelic, phthalic, trimellitic, terephthalic and salicylic acids as well as (in the case of diacids) any of their respective anhydrides, half-esters and half-amides.

Other suitable carboxylate initiators include aliphatic dicarboxylic acids such as adipic, aldaric, fumaric, glutaric, maleic, malic, malonic, oxalic, succinic, dodecenyl succinic, octadecenyl succinic, citraconic, tetrahydrophthalic, methyltetrahydrophthalic, hexahydrophthalic, alkyl hexahydrophthalic, tetrachlorophthalic itaconic and tartronic acids, as well as their respective anhydrides, half-esters and half-amides.

Still other suitable carboxylate initiators include tricarboxylic acids such as citric, isocitric, aconitic, and propane-1,2,3-tricarboxylic acid, as well as anhydrides, partial esters and partial amides of any thereof.

Hydroxyacids, such as glyceric, glycolic, lactic and tartaric acids are also useful carboxylate initiators.

Still other suitable carboxylate initiators include unsaturated monocarboxylic acids such as acrylic and methacrylic acids; halide-containing acids such as chloroacetic, dichloroacetic, trichloroacetic, and trifluoroacetic acids, and amino acids such as aminoethanoic, aminopropanoic, aminobutanedioic, aminopentanedioic and ethylenediaminetetraacetic acids.

Also useful as the carboxylate initiator are carboxyl group-containing compounds that are obtained from renewable resources. These include, for example, amino acids and fatty acids obtained from animal and/or plant sources.

Other suitable carboxylate initiators are half acid esters formed in the reaction of a carboxylic acid anhydride compound with a polyol compound. The polyol compound contains at least two hydroxyl groups and may contain any greater number of hydroxyl groups. It preferably contains 2 to 12, more preferably 2 to 6, still more preferably 2 to 4 hydroxyl groups. The polyol may be, for example, polyester polyol, a polyether-polyester polyol, or a polyether polyol, such as ethylene glycol, diethylene glycol, propylene glycol, dipropylene glycol, 1,3-propanediol, 1,4-butanediol; 1,5-pentanediol, 1,6-hexanediol, 1,4-cyclohexanedimethanol, 1,8-octanediol; neopentyl glycol; 1-3 butanediol; 2,2,4-trimethyl-1,3-pentanediol, dimethylolpropane, glycerine, trimethylolpropane, trimethylolethane, pentaerythritol, 1,2,4-butanetriol, 1,2,6-hexanetriol, erythritol, xylitol, sorbitol and the like.

Still other carboxylate initiators are half acid amides formed in the reaction of a carboxylic acid anhydride compound with an amine such as ethanol methyl amine, 3-propanol methyl amine, 2-propanol methyl amine, bis-(2-hydroxypropyl)amine, triethanolamine, diethanolamine, N,N' dimethyl ethylenediamine, N,N' dimethyl butylene diamine, N,N' dimethyl toluenediamine, or N,N' dimethyl phenylenediamine and the like.

Any of the foregoing half-ester compounds can be formed in situ performing the polymerization of the alkylene oxide in the presence of the corresponding carboxylic acid anhydride and polyol compounds. The anhydride compound and polyol compounds can react to form the half-ester during the polymerization step.

The alkylene oxide may be, for example, ethylene oxide, 1,2-propylene oxide, 2,3-propylene oxide, 1,2-butane oxide, 2,3-butane oxide, 2-methyl-1,2-butane oxide, tetrahydrofuran, epichlorohydrin, hexane oxide, styrene oxide, divinylbenzene dioxide, a glycidyl ether such as bisphenol A diglycidyl ether, or other polymerizable oxirane. The preferred alkylene oxide by far is 1,2-propylene oxide, or a mixture of at least 50% (preferably at least 80%) by weight propylene oxide and up to 50% (preferably up to 20%) ethylene oxide.

Suitable double metal cyanide catalysts include those described, for example, in U.S. Pat. Nos. 3,278,457, 3,278,458, 3,278,459, 3,404,109, 3,427,256, 3,427,334, 3,427,335 and 5,470,813. Some suitable DMC catalysts can be represented by the formula

$$M_b[M^1(CN)_r(X)_t]_c[M^2(X)_6]_d \cdot nM^3_xA_y$$

wherein M and $M^3$ are each metals; $M^1$ is a transition metal different from M, each X represents a group other than cyanide that coordinates with the $M^1$ ion; $M^2$ is a transition metal; A represents an anion; b, c and d are numbers that reflect an electrostatically neutral complex; r is from 4 to 6; t is from 0 to 2; x and y are integers that balance the charges in the metal salt $M^3_xA_y$, and n is zero or a positive integer. The foregoing formula does not reflect the presence of neutral complexing agents such as t-butanol which are often present in the DMC catalyst complex.

M and $M^3$ each are preferably a metal ion independently selected from the group consisting of $Zn^{2+}$, $Fe^{2+}$, $Co^{+2+}$, $Ni^{2+}$, $Mo^{4+}$, $Mo^{6+}$, $Al^{+3+}$, $V^{4+}$, $V^{5+}$, $Sr^{2+}$, $W^{4+}$, $W^{6+}$, $Mn^{2+}$, $Sn^{2+}$, $Sn^{4+}$, $Pb^{2+}$, $Cu^{2+}$, $La^{3+}$ and $Cr^{3+}$, with $Zn^{2+}$ being preferred. $M^1$ and $M^2$ are preferably $Fe^{3+}$, $Fe^{2+}$, $Co^{3+}$, $Co^{2+}$, $Cr^{2+}$, $Cr^{3+}$, $Mn^{2+}$, $Mn^{3+}$, $Ir^{3+}$, $Ni^{2+}$, $Rh^{3+}$, $Ru^{2+}$, $V^{4+}$, $V^{5+}$, $Ni^{2+}$, $Pd^{2+}$, and $Pt^{2+}$. Among the foregoing, those in the plus-three oxidation state are more preferred as the $M^1$ and $M^2$ metal. $Co^{+3}$ and $Fe^{+3}$ are even more preferred and $Co^{+3}$ is most preferred.

Suitable anions A include but are not limited to halides such as chloride, bromide and iodide, nitrate, sulfate, carbonate, cyanide, oxalate, thiocyanate, isocyanate, perchlorate, isothiocyanate, an alkanesulfonate such as methanesulfonate, an arylenesulfonate such as p-toluenesulfonate, trifluoromethanesulfonate (triflate) and a $C_{1-4}$ carboxylate. Chloride ion is especially preferred.

r is preferably 4, 5 or 6, preferably 4 or 6, and most preferably 6; t is preferably 0 or 1, most preferably 0. In most cases, r+t will equal six.

A suitable type of DMC catalyst is a zinc hexacyanocobaltate catalyst complex as described, for example, in any of U.S. Pat. Nos. 3,278,457, 3,278,458, 3,278,459, 3,404,109, 3,427,256, 3,427,334, 3,427,335 and 5,470,813. An especially preferred type of DMC catalyst is complexed with t-butanol.

The MG3-15LA compound is a separately added ingredient, which is not present during the preparation (i.e., the precipitation step) of the DMC catalyst complex. The mechanism by which the MG3-15LA compound provides benefits to the polymerization is not fully understood. Although the invention is not bound by any theory, it is possible that some reaction or other interaction between this compound and the DMC catalyst complex takes place.

The MG3-15LA compound contains a magnesium, Group 3-Group 15 metal or lanthanide series metal ion bonded to at least one alkoxide, aryloxy, carboxylate, acyl, pyrophosphate, phosphate, thiophosphate, dithiophosphate, phosphate ester, thiophosphate ester amide, siloxide, hydride, carbamate or hydrocarbon anion. The MG3-15LA compound is devoid of halide anions.

By "alkoxide ion" it is meant a species having the form $^-O$—R, where R is an alkyl group or substituted alkyl group, and which is the conjugate base, after removal of a hydroxyl hydrogen, of an alcohol compound having the form HO—R. These alcohols typically have pKa values in the range of 13 to 25 or greater. The alkoxide ion in some embodiments may contain from one to 20, more preferably from one to 6 and still more preferably from 2 to 6 carbon atoms. The alkyl group or substituted alkyl group may be linear, branched and/or cyclic. Examples of suitable substituents include, for example, additional hydroxyl groups (which may be in the alkoxide form), ether groups, carbonyl groups, ester groups, urethane groups, carbonate groups, silyl groups, aromatic groups such as phenyl and alkyl-substituted phenyl, halogen, and the like. Examples of such alkoxide ions include methoxide, ethoxide, isopropoxide, n-propoxide, n-butoxide, sec-butoxide, t-butoxide, benzyloxy, and the like. In other embodiments, the R group may contain one or more hydroxyl groups and/or may contain one or more ether linkages. An alkoxide ion may correspond to the residue (after removal of one or more hydroxyl hydrogens) of an initiator compound that is present in the polymerization, such as those initiator compounds described below. The alkoxide ion may be an alkoxide formed by removing one or more hydroxyl hydrogens from a polyether monol or polyether polyol; such an alkoxide in some embodiments corresponds to a residue, after removal of one or more hydroxyl hydrogen atoms, of the polyether monol or polyether polyol product that is obtained from the alkoxylation reaction, or of a polyether having a molecular weight intermediate to that of the initiator compound and the product of the alkoxylation reaction.

By "aryloxy anion" it is meant a species having the form $^-O$—Ar, where Ar is an aromatic group or substituted group, and which corresponds, after removal of a hydroxyl hydrogen, to a phenolic compound having the form HO—Ar. These phenolic compounds may have a pKa of, for example, from about 9 to about 12. Examples of such aryloxy anions include peroxide and ring-substituted peroxides, wherein the ring-substituents include, for example, alkyl, $CF_3$, cyano, $COCH_3$, halogen, hydroxyl, alkoxyl and the like. The ring-substituent(s) if present, may be in one or more of the ortho-, para- and/or meta-positions relative to the phenolic group. The phenoxide anions also include the conjugate bases of polyphenolic compounds such as bisphenol A, bisphenol F and various other bisphenols, 1,1,1-tris(hydroxyphenyl) ethane, and fused ring aromatics such as 1-naphthol and the like.

A carboxylate anion preferably contains from one to 24, more preferably from 2 to 18 and still more preferably from 2 to 12 carbon atoms. It may be aliphatic or aromatic. An aliphatic carboxylic acid may contain substituent groups such as hydroxyl groups (which may be in the alkoxide form), ether groups, carbonyl groups, ester groups, urethane groups, carbonate groups, silyl groups, aromatic groups such as phenyl and alkyl-substituted phenyl, halogen, and the like.

Examples of aliphatic carboxylate anions include formate, acetate, propionate, butyrate, 2-ethylhexanoate, n-octoate, decanoate, laurate and other alkanoates and halogen-substituted alkanoates such as 2,2,2-trifluoroacetate, 2-fluoroacetate, 2,2-difluoroacetate, 2-chloroacetate, 2,2,2-trichloroacetate and the like. Aromatic carboxylates include benzoate, alkyl-substituted benzoate, halo-substituted benzoate, 4-cyanobenzoate, 4-trifluoromethylbenzoate, salicylate, 3,5-di-t-butylsalicylate, subsalicylate, and the like. In some embodiments, such a carboxylate ion may be the conjugate base of a carboxylic acid having a pKa from 1 to 6, preferably from 3 to 5.

By "acyl anion", it is meant a conjugate base of a compound containing a carbonyl group including, for example, an aldehyde, ketone, carbonate, ester or similar compound which has an enol form. Among these are β-diketo compounds, such as acetoacetonate, butylacetoacetonate and the like.

Phosphate ester anions include those having the formula $^-$O—P(O)(OR$^1$)$_2$, wherein R is alkyl, substituted alkyl, phenyl or substituted phenyl. Thiophosphate esters have the corresponding structure in which one or more of the oxygens is replaced with sulfur.

By "amide anion", it is meant an ion in which a nitrogen atom bears a negative charge. The amide ion generally takes the form $^-$N(R$^2$)$_2$, wherein the R$^2$ groups are independently hydrogen, alkyl, aryl, trialkylsilyl, triarylsilyl and the like. The alkyl groups may be linear, branched or cyclic. Any of these groups may contain substituents such as ether or hydroxyl. The two R$^2$ groups may together form a ring structure, which ring structure may be unsaturated and/or contain one or more heteroatoms (in addition to the amide nitrogen) in the ring.

Hydrocarbyl anions include aliphatic, cycloaliphatic and/or aromatic anions wherein the negative charge resides on a carbon atom. The hydrocarbyl anions are conjugate bases of hydrocarbons that typically have pKa values in excess of 30. The hydrocarbyl anions may also contain inert substituents. Of the aromatic hydrocarbyl anions, phenyl groups and substituted phenyl groups are preferred. Aliphatic hydrocarbyl anions are preferably alkyl groups, which more preferably contain from 1 to 12, more preferably from 2 to 8 carbon atoms. Methyl, ethyl, n-propyl, isopropyl, n-butyl, sec-butyl, isobutyl, cyclopentadienyl and t-butyl anions are all useful, for example.

Preferred anions are the conjugate base of a compound having a pKa of at least 1.5, preferably at least 2.5, still more preferably at least 3.0. The pKa of the conjugate acid has been found in some cases to relate to the time required to activate the DMC catalyst complex in a polymerization process of this invention. It has been found that shorter activation times are generally seen when the anions correspond to the conjugate base of a compound having a pKa of at least 9, preferably at least 12, more preferably at least 13. The anion may be the conjugate base of a compound having any higher pKa, such as up to 60 or higher. Anions corresponding to the conjugate base of a compound having a pKa of less than 9, especially less than 5, often have been found to lead to longer activation times. Therefore, especially preferred anions are alkoxide, aryloxy, amide, and hydrocarbyl anions which are the conjugate base of a compound having a pKa of at least 9, more preferably at least 12 and still more preferably at least 13, up to 60 or greater.

The Group 3-Group 15 metals are metals falling within any of groups III through 15, inclusive, of the 2010 IUPAC periodic table of the elements. The metal may be, for example, scandium, yttrium, lanthanum, titanium, zirconium, hafnium, vanadium, niobium, tantalum, chromium, molybdenum, tungsten, manganese, rhenium, iron, ruthenium, osmium, cobalt, rhodium, iridium, nickel, palladium, platinum, copper, silver, gold, zinc, cadmium, mercury, aluminum, gallium, indium, tellurium, germanium, tin, lead, antimony, bismuth, lanthanum and the lanthanide series metals include those having atomic number from 58 (cerium) to 71 (lutetium), inclusive.

Preferred metals include those in Groups 3, 4, 5, 12, 13 and 14. Among these, magnesium, scandium, yttrium, hafnium, titanium, zirconium, niobium, vanadium, zinc, aluminum, gallium, indium and tin are more preferred, as these metals tend to provide fast polymerization rates and/or allow very small quantities of the DMC catalyst to be present. Aluminum, gallium, indium, zinc, hafnium, tin, titanium and zirconium are especially preferred.

Among the suitable MG3-15LA compounds are those corresponding to either of the formulae M$^4$A$^1$z and M$^4$(O)A$^1_z$, wherein M$^4$ is the magnesium, Group 3-Group 15 metal or lanthanide series metal, each A$^1$ is independently an anion as described before and z is a number of at least one which reflects an electrostatically neutral compound, provided that any two or more A$^1$ groups may together form a polyvalent group. Each A$^1$ preferably is independently an alkoxide, aryloxy anion, amide, anion or hydrocarbyl anion that is the conjugate base of a compound having a pKa of at least 9, more preferably at least 12 and still more preferably at least 13. As before, any A$^1$ may be an alkoxide anion which is the conjugate base of an initiator compound or a polyether monol or polyether polyol, including the polyether monol or polyether polyol product that is obtained from the alkoxylation reaction or a polyether having a molecular weight intermediate to that of the initiator compound and the product of the alkoxylation reaction.

The MG3-15LA compound is preferably devoid of anions that are conjugate bases of inorganic acids such as sulfate, sulfite, persulfate, nitrate, nitrite, chlorate, perchlorate, hypochlorite, carbonate, chromate, and the like; sulfonate anions such as trifluoromethylsulfonate and methyl sulfonate; and hydroxide ions.

Examples of suitable MG3-15LA compounds include but are not limited to:

a) magnesium alkyls such as diethyl magnesium, dibutyl magnesium, butylethyl magnesium, dibenzyl magnesium and the like; magnesium alkoxides such as magnesium methoxide, magnesium ethoxide, magnesium isopropoxide, magnesium t-butoxide, magnesium sec-butoxide and the like; magnesium aryloxides such as magnesium phenoxide, and magnesium phenoxides in which one or more of the phenoxide groups is ring-substituted with alkyl, CF$_3$, cyano, COCH$_3$, halogen, hydroxyl, alkoxyl and the like; magnesium carboxylates such as magnesium formate, magnesium acetate, magnesium propionate, magnesium 2-ethylhexanoate, magnesium benzoate, magnesium benzoates in which one or more of the benzoate groups is ring-substituted with alkyl, CF$_3$, cyano, COCH$_3$, halogen, hydroxyl, alkoxyl and the like, magnesium salicylate, magnesium 3,5-di-t-butyl salicylate; magnesium amides such as magnesium dimethylamide, magnesium diethylamide, magnesium diphenylamide, magnesium bis(trimethylsilyl)amide and the like; magnesium acetylacetonate and magnesium t-butylacetylacetonate.

b) scandium alkoxides such as scandium methoxide, scandium ethoxide, scandium isopropoxide, scandium t-butoxide, scandium sec-butoxide and the like; scandium aryloxides such as scandium phenoxide and scandium phenoxides in which one or more of the phenoxide groups is ring-substituted with alkyl, CF$_3$, cyano, COCH$_3$, halogen, hydroxyl, alkoxyl and the like; scandium carboxylates such as scandium formate, scandium acetate, scandium propionate, scandium 2-ethylhexanoate, scandium benzoate, scandium benzoates in which one or more of the benzoate groups is ring-substituted with alkyl, $CF_3$, cyano, $COCH_3$, halogen, hydroxyl, alkoxyl and the like; scandium salicylate; scandium acetylacetonate and scandium t-butylacetylacetonate.

c) yttrium alkoxides such as yttrium methoxide, yttrium ethoxide, yttrium isopropoxide, yttrium t-butoxide, yttrium sec-butoxide and the like; yttrium aryloxides such as yttrium phenoxide, and yttrium phenoxides in which one or more of the phenoxide groups is ring-substituted with alkyl, $CF_3$, cyano, $COCH_3$, halogen, hydroxyl, alkoxyl and the like; yttrium carboxylates such as yttrium formate, yttrium acetate, yttrium propionate, yttrium 2-ethylhexanoate, yttrium benzoate, yttrium benzoates in which one or more of the benzoate groups is ring-substituted with alkyl, $CF_3$, cyano, $COCH_3$, halogen, hydroxyl, alkoxyl and the like, yttrium salicylate, yttrium 3,5-di-t-butyl salicylate; yttrium amides such as yttrium dimethylamide, yttrium diethylamide, yttrium diphenylamide, yttrium bis(trimethylsilyl)amide and the like; yttrium acetylacetonate and yttrium t-butylacetylacetonate.

d) hafnium alkyls such as such as tetraethyl hafnium, tetrabutyl hafnium, tetrabenzyl hafnium and the like; hafnium alkoxides such as hafnium tetramethoxide, hafnium tetraethoxide, hafnium tetraisopropoxide, hafnium tetra-t-butoxide, hafnium tetra-sec-butoxide and the like; hafnium aryloxides such as hafnium phenoxide and hafnium phenoxides in which one or more of the phenoxide groups is ring-substituted with alkyl, $CF_3$, cyano, $COCH_3$, halogen, hydroxyl, alkoxyl and the like; hafnium carboxylates such as hafnium formate, hafnium acetate, hafnium propionate, hafnium 2-ethylhexanoate, hafnium benzoate, hafnium benzoates in which one or more of the benzoate groups is ring-substituted with alkyl, $CF_3$, cyano, $COCH_3$, halogen, hydroxyl, alkoxyl and the like, hafnium salicylate, hafnium 3,5-di-t-butyl salicylate; hafnium amides such as hafnium tetra(dimethylamide), hafnium tetra(diethylamide), hafnium tetra(diphenylamide), hafnium tetra((bistrimethylsilyl)amide); hafnium acetylacetonate and hafnium t-butylacetylacetonate;

e) titanium alkyls such as such as tetraethyl titanium, tetrabenzyl titanium and the like; titanium alkoxides such as titanium tetramethoxide, titanium tetraethoxide, titanium tetraisopropoxide, titanium tetra-t-butoxide, titanium tetra-sec-butoxide and the like; titanium aryloxides such as titanium phenoxide and titanium phenoxides in which one or more of the phenoxide groups is ring-substituted with alkyl, $CF_3$, cyano, $COCH_3$, halogen, hydroxyl, alkoxyl and the like; titanium carboxylates such as titanium formate, titanium acetate, titanium propionate, titanium 2-ethylhexanoate, titanium benzoate, titanium benzoates in which one or more of the benzoate groups is ring-substituted with alkyl, $CF_3$, cyano, $COCH_3$, halogen, hydroxyl, alkoxyl and the like, titanium salicylate, titanium 3,5-di-t-butyl salicylate; titanium amides such as titanium tetra(dimethylamide), titanium tetra(diethylamide, titanium tetra(diphenylamide), titanium tetra((bistrimethylsilyl)amide); titanium acetylacetonate and titanium t-butylacetylacetonate;

f) zirconium alkyls such as such as tetraethyl zirconium, tetrabutyl zirconium, tetrabenzyl zirconium and the like; zirconium alkoxides such as zirconium tetramethoxide, zirconium tetraethoxide, zirconium tetraisopropoxide, zirconium tetra-t-butoxide, zirconium tetra-sec-butoxide and the like; zirconium aryloxides such as zirconium phenoxide and zirconium phenoxides in which one or more of the phenoxide groups is ring-substituted with alkyl, $CF_3$, cyano, $COCH_3$, halogen, hydroxyl, alkoxyl and the like; zirconium carboxylates such as zirconium formate, zirconium acetate, zirconium propionate, zirconium 2-ethylhexanoate, zirconium benzoate, zirconium benzoates in which one or more of the benzoate groups is ring-substituted with alkyl, $CF_3$, cyano, $COCH_3$, halogen, hydroxyl, alkoxyl and the like, zirconium salicylate, zirconium 3,5-di-t-butyl salicylate; zirconium amides such as zirconium tetra(dimethylamide), zirconium tetra(diethylamide, zirconium tetra(diphenylamide), zirconium tetra((bistrimethylsilyl)amide); zirconium acetylacetonate and zirconium t-butylacetylacetonate;

g) vanadium alkoxides such as vanadium methoxide, vanadium ethoxide, vanadium isopropoxide, vanadium t-butoxide, vanadium sec-butoxide and the like; vanadium oxo tris (alkoxides) such as vanadium oxo tris(methoxide), vanadium oxo tris(ethoxide), vanadium oxo tris(isopropoxide), vanadium oxo tris(t-butoxide), vanadium oxo tris(sec-butoxide) and the like; vanadium aryloxides such as vanadium phenoxide and vanadium phenoxides in which one or more of the phenoxide groups is ring-substituted with alkyl, $CF_3$, cyano, $COCH_3$, halogen, hydroxyl, alkoxyl and the like; vanadium carboxylates such as vanadium formate, vanadium acetate, vanadium propionate, vanadium 2-ethylhexanoate, vanadium benzoate, vanadium benzoates in which one or more of the benzoate groups is ring-substituted with alkyl, $CF_3$, cyano, $COCH_3$, halogen, hydroxyl, alkoxyl and the like, vanadium salicylate, vanadium 3,5-di-t-butyl salicylate; vanadium tris (acetylacetonate) and vanadium tris(t-butylacetylacetonate); vanadium oxo bis(acetylacetonate);

h) zinc alkyls such as such as dimethyl zinc, diethyl zinc, dibutyl zinc, dibenzyl zinc and the like; alkyl zinc alkoxides such as ethyl zinc isopropoxide; zinc alkoxides such as zinc methoxide, zinc ethoxide, zinc isopropoxide, zinc t-butoxide, zinc sec-butoxide and the like; zinc aryloxides such as zinc phenoxide and zinc phenoxides in which one or more of the phenoxide groups is ring-substituted with alkyl, $CF_3$, cyano, $COCH_3$, halogen, hydroxyl, alkoxyl and the like; zinc carboxylates such as zinc formate, zinc acetate, zinc propionate, zinc 2-ethylhexanoate, zinc benzoate, zinc benzoates in which one or more of the benzoate groups is ring-substituted with alkyl, $CF_3$, cyano, $COCH_3$, halogen, hydroxyl, alkoxyl and the like, zinc salicylate, zinc 3,5-di-t-butyl salicylate; zinc amides such as zinc dimethylamide, zinc diethylamide, zinc diphenylamide, zinc (bistrimethylsilyl)amide; zinc acetylacetonate and zinc t-butylacetylacetonate;

i) trialkyl aluminum compounds such as trimethylaluminum, triethyl aluminum, tributyl aluminum, tribenzylaluminum and the like; aluminum alkoxides such as aluminum trimethoxide, aluminum triethoxide, aluminum triisopropoxide, aluminum tri-t-butoxide, aluminum tri-sec-butoxide and the like; aluminum aryloxides such as aluminum phenoxide and aluminum phenoxides in which one or more of the phenoxide groups is ring-substituted with alkyl, $CF_3$, cyano, $COCH_3$, halogen, hydroxyl, alkoxyl and the like; aluminum carboxylates such as aluminum formate, aluminum acetate, aluminum propionate, aluminum 2-ethylhexanoate, aluminum benzoate, aluminum benzoates in which one or more of the benzoate groups is ring-substituted with alkyl, $CF_3$, cyano, $COCH_3$, halogen, hydroxyl, alkoxyl and the like, aluminum salicylate, aluminum 3,5-di-t-butyl salicylate; aluminum amides such as aluminum, tris(dimethylamide), aluminum tris(diethylamide), aluminum tris(diphenylamide), aluminum tris(di(trimethylsilyl)amide) and the like; aluminum acetylacetonate; aluminum t-butylacetylacetonate; and alkylaluminum oxides and alkoxides such as diethylaluminum ethoxide, dimethylaluminum ethoxide, diethylaluminum isopropoxide, dimethylaluminum isopropoxide, methyl aluminoxane, tetraethyldialuminoxane and the like;

j) trialkyl gallium compounds such as trimethylgallium, triethyl gallium, tributyl gallium, tribenzylgallium and the like; gallium alkoxides such as gallium trimethoxide, gallium triethoxide, gallium triisopropoxide, gallium tri-t-butoxide, gallium tri-sec-butoxide and the like; gallium aryloxides such as gallium phenoxide and gallium phenoxides in which one or more of the phenoxide groups is ring-substituted with alkyl, $CF_3$, cyano, $COCH_3$, halogen, hydroxyl, alkoxyl and the like; gallium carboxylates such as gallium formate, gallium acetate, gallium propionate, gallium 2-ethylhexanoate, gallium benzoate, gallium benzoates in which one or more of the benzoate groups is ring-substituted with alkyl, $CF_3$, cyano, $COCH_3$, halogen, hydroxyl, alkoxyl and the like, gallium salicylate, gallium 3,5-di-t-butyl salicylate; gallium amides such as gallium tris(dimethylamide), gallium tris(diethylamide), gallium tris(diphenylamide), gallium tris(di(trimethylsilyl)amide) and the like; gallium acetylacetonate; gallium t-butylacetylacetonate; and alkylgallium alkoxides such as diethylgallium ethoxide, dimethylgallium ethoxide, diethylgallium isopropoxide and dimethylgallium isopropoxide;

k) trialkyl indiums compounds such as trimethylindium; indium alkoxides such as indium methoxide, indium ethoxide, indium isopropoxide, indium t-butoxide, indium sec-butoxide and the like; indium aryloxides such as indium phenoxide and indium phenoxides in which one or more of the phenoxide groups is ring-substituted with alkyl, $CF_3$, cyano, $COCH_3$, halogen, hydroxyl, alkoxyl and the like; indium carboxylates such as indium formate, indium acetate, indium propionate, indium 2-ethylhexanoate, indium benzoate, indium benzoates in which one or more of the benzoate groups is ring-substituted with alkyl, $CF_3$, cyano, $COCH_3$, halogen, hydroxyl, alkoxyl and the like, indium salicylate, indium 3,5-di-t-butyl salicylate; indium acetylacetonate; and indium t-butylacetylacetonate;

l) stannous phosphate; stannous pyrophosphate, stannous alkoxides such as stannous methoxide, stannous ethoxide, stannous isopropoxide, stannous t-butoxide, stannous sec-butoxide and the like; stannous aryloxides such as stannous phenoxide and stannous phenoxides in which one or more of the phenoxide groups is ring-substituted with alkyl, $CF_3$, cyano, $COCH_3$, halogen, hydroxyl, alkoxyl and the like; stannous carboxylates such as stannous formate, stannous acetate, stannous propionate, stannous 2-ethylhexanoate, stannous benzoate, stannous benzoates in which one or more of the benzoate groups is ring-substituted with alkyl, $CF_3$, cyano, $COCH_3$, halogen, hydroxyl, alkoxyl and the like, stannous salicylate, stannous 3,5-di-t-butyl salicylate; stannous acetylacetonate; and stannous t-butylacetylacetonate.

In addition to the foregoing, other suitable MG3-15LA compounds include magnesium, Group 3-Group 15 metal or lanthanide series metal alkoxides one or more of the alkoxide group(s) are the conjugate base, after removal of one or more hydroxyl hydrogen atoms, from (1) an initiator compound as described below, (2) a polyether monol or polyether polyol product of the polymerization reaction or (3) a polyether having a molecular weight intermediate to the initiator and the polyether monol or polyether polyol product of the polymerization.

If desired, mixtures of two or more of the foregoing MG3-15LA compounds may be used.

In the present invention, an alkylene oxide is polymerized in the presence of the carboxylate initiator compound, the DMC catalyst complex and the MG3-15LA compound, or a catalyst mixture formed by combining the DMC catalyst complex and the MG3-15LA compound. In some embodiments, enough of the MG3-15LA compound is present to provide at least 0.0005 moles of magnesium, group 3-group 15 metal or lanthanide series metal compound per gram of the DMC catalyst complex. A preferred amount is enough to provide at least 0.0025 or at least 0.005 moles of the magnesium, group 3-group 15 metal or lanthanide series metal per gram of the DMC catalyst complex. It is generally not necessary to provide more than 10 moles of magnesium, group 3-group 15 metal or lanthanide series metal compound per gram of the DMC catalyst complex. A preferred upper limit is enough to provide up to 1 mole, up to 0.5 moles or up to 0.25 moles of magnesium, group 3-group 15 metal or lanthanide series metal compound per gram of DMC catalyst complex. The foregoing amounts do not include any amounts of metals that are included within the DMC catalyst complex.

Enough of the catalyst mixture is used to provide a reasonable polymerization rate. It is generally desirable to use as little of the double metal cyanide catalyst as possible consistent with reasonable polymerization rates, as this both reduces the cost for the catalyst and, if the catalyst levels are low enough, can eliminate the need to remove catalyst residues from the product. The amount of DMC catalyst complex may be from 1 to 5000 ppm based on the weight of the product. The amount of DMC catalyst complex may be at least 2 ppm, at least 5 ppm, at least 10 ppm, at least 25 ppm, or up to 200 ppm or up to 100 ppm, based on the weight of the product.

The polymerization of the alkylene oxide is suitably performed at an elevated temperature such as at least 80° C., preferably at least 120° C., and more preferably at least 140° C. The reaction temperature may be 200° C. or higher, but it is preferred that the temperature does not exceed 190° C., more preferably 180° C., in order to maintain workable reactor pressures, to avoid forming a significant amount of volatile impurities or other by-products, and to maintain adequate catalyst activity without deactivating or decomposing the DMC catalyst. The polymerization reaction usually is performed at superatmospheric pressures, but can be performed at atmospheric pressure or even subatmospheric pressures.

The polymerization may be performed in the presence of a solvent such as toluene or xylene. If used, the amount of such solvent is desirably minimized and may range from 10 to 50 percent (%), more desirably from 25 to 35%, based on the total weight of the carboxylate initiator (or precursor(s)).

The polymerization reaction can be performed batch-wise, semi-continuously (including with continuous addition of starter as described in U.S. Pat. No. 5,777,177) or continuously. In a batch polymerization, the DMC catalyst complex, all of the MG3-15LA compound, alkylene oxide and carboxylate initiator (or precursor(s) to the carboxylate initiator(s)) are charged to a reaction vessel and heated to the polymerization temperature until the desired molecular weight is obtained.

In a semi-batch process, DMC catalyst complex, MG3-15LA compound and carboxylate initiator (or precursor(s) to the carboxylate initiator(s)) are combined. A portion of the alkylene oxide is introduced into the reaction vessel and the contents of the vessel are heated if necessary to the polymerization temperature. When the DMC catalyst complex has become activated (typically as indicated by a drop of internal reactor pressure), more alkylene oxide is fed to the reactor under polymerization conditions. The alkylene oxide feed is continued until enough has been consumed to reach the target product molecular weight. Additional DMC catalyst and/or MG3-15LA compound may be added during the course of the alkylene oxide addition. In a semi-batch process, the entire amount of initiator or precursor(s) thereto is commonly added at the start of the process. After the alkylene oxide feed is completed, the reaction mixture may be cooked down at the polymerization temperature to consume any remaining alkylene oxide.

A continuous polymerization includes the continuous addition of alkylene oxide and initiator and the continuous removal of product. A continuous polymerization is generally conducted by establishing steady-state concentrations, within the operational capabilities of the polymerization equipment, of the DMC catalyst, the MG3-15LA compound, carboxylate initiator (or precursor(s) to the carboxylate initiator(s)), alkylene oxide and polymerizate under polymerization conditions in a continuous reactor such as a loop reactor or a continuous stirred tank reactor. The "polymerizate" is a mixture of polyethers that have molecular weights greater than that of the initiator and up to that of the intended product. Additional DMC catalyst complex, MG3-15LA compound, initiator (or precursor(s)) and alkylene oxide are then continuously added to the reactor. These can be added as a single stream, as separate components, or in various sub-combinations. Additional catalyst mixture can be formed by combining the DMC catalyst complex with the MG3-15LA compound, optionally with the initiator compound, and added during the polymerization. A product stream is continuously withdrawn from the reactor. The rates of the additional stream(s) and product streams typically are selected to maintain steady-state conditions in the reactor (within the capabilities of the equipment), and to produce a product having a desired molecular weight. The product stream withdrawn from the continuous reactor may be cooked down for some period of time to allow the unreacted alkylene oxide in that stream to be consumed to low levels.

In some embodiments of the invention, the initiator is formed from one or more precursor(s) and the polymerization performed in a single-step process. The precursor(s) in such a case may be, for example, a carboxylic acid anhydride, or a mixture of a carboxylic acid anhydride and a polyol compound. Therefore, in one embodiment of the invention, a carboxylic acid anhydride, DMC catalyst complex, MG3-15LA compound and alkylene oxide are subjected to polymerization conditions, and the alkylene oxide polymerized. The carboxylic acid anhydride opens during the reaction to form a carboxylic acid that functions as the initiator. In another embodiment of the invention, a carboxylic acid anhydride, polyol compound, DMC catalyst complex, MG3-15LA compound and alkylene oxide are combined and subjected to polymerization conditions, and the alkylene oxide polymerized. The carboxylic acid anhydride and polyol react to form a half-ester to form a carboxylic acid that functions as the initiator.

In alternative embodiments of the invention, precursor(s) to the carboxylate initiator are first reacted to form the initiator, followed by polymerization of the alkylene oxide. This two-step process is suitable, for example, for (a) forming a carboxylic acid carboxylate initiator by ring-opening a carboxylic acid anhydride, (b) forming a half-ester carboxylate initiator through reaction of a carboxylic acid anhydride and a polyol, and (c) forming a half-amide carboxylate initiator through reaction of a carboxylic acid anhydride and an amine compound. The two steps can be performed in a single apparatus. Some or all of the alkylene oxide can be present in the first step, but if so, it is preferred that the MG3-15LA compound, and preferably both the MG3-15LA compound and the DMC catalyst complex, are absent in the first step. It is also possible to perform the first step by mixing the precursor(s), alkylene oxide, DMC catalyst complex and MG3-15LA compound, and forming the carboxylate initiator before the alkylene oxide begins to polymerize. For example, in the two-step process, the carboxylate initiator may form before the DMC catalyst becomes activated and the alkylene oxide begins to polymerize.

The product of the polymerization is a hybrid polyester-polyether polyol that contains both ester and ether groups, as well as one or more hydroxyl groups. The number of hydroxyl groups per molecule is approximately fixed by the number of sites on the carboxylate initiator at which alkoxylation can occur. The product, for example, may contain from 1 to 16, more preferably 2 to 8, still more preferably 2 to 6 and still more preferably 2 to 4 hydroxyl groups per molecule. The hydroxyl equivalent of the product may range, for example, from 100 to 5,000 or more.

The product may have polydispersity index less of than 1.5, less than 0.01 meq/g of terminal unsaturation, and an acid number less than 2.0 mg/g as potassium hydroxide.

The final hybrid polyester-polyether product may be used for (among other things) producing a polyurethane through reaction with a polyisocyanate. Among the polyurethanes that can be made include flexible and rigid foams for applications such as insulation for purposes such as for appliances and construction, as well as polyurethane elastomers and polyurethane adhesives.

The following examples are provided to illustrate the invention but are not intended to limit the scope thereof. All parts and percentages are by weight unless otherwise indicated.

EXAMPLE 1

1173.0 g (2.60 mol) of a propoxylate of glycerin that has an average molecular weight of 450 (VORANOL CP450 polyol, The Dow Chemical Company) and 384.0 g (2.60 mol) phthalic anhydride are added to a reactor. The reaction mixture is flushed 10 times with nitrogen. The reactor is thermostated at 100° C. with 6 bar of $N_2$ pressure and stirring. The materials gradually dissolve in the reactor, becoming mainly liquid after 1 hour. The reactor content is stirred for additional 15 hours. The $N_2$ pressure in the reactor is reduced to 100 kPa and the temperature is increased to 130° C. Propylene oxide (385.0 g, 6.63 mol) is fed to the reactor at an average feed rate of 5.5 g/min over 70 minutes. At the completion of the feed the total pressure in the reactor has reached 490 kPa. The reaction mixture is digested for one hour at 130° C., during which time the pressure in the reactor decreases to 400 kPa. A 268.0 g sample is taken, from which unreacted propylene oxide is stripped under vacuum.

Solid DMC catalyst complex (0.346 g) is dispersed in the stripped polyol sample. The dispersion contains 1290 ppm of the DMC catalyst. 66.6 g of this DMC catalyst dispersion is injected back into the reactor, followed by a feed of additional 70 g (1.21 mol) of propylene oxide. After the propylene oxide feed is completed, the reaction mixture is stirred for 1 hour at 130° C. No activation of the DMC catalyst activation is observed.

An additional 91.4 g of the DMC catalyst dispersion is injected into the reactor, followed by a feed of additional 20 g of propylene oxide. No catalyst activation is observed, even after stirring the reaction mixture for another hour at 130° C.

The reactor temperature is increased to 140° C. The remaining 110.0 g of the DMC catalyst dispersion is mixed with 1.41 g of aluminum isobutoxide and injected into the reactor. Smooth DMC catalyst activation, accompanied by a pressure drop in the reactor and an exotherm, is observed within 10 minutes following the injection. An additional 1152 g (19.83 mol) of PO are fed to the reactor at 30 g/minute, followed by an additional 0.5 hour of digestion time. A colorless viscous liquid is obtained.

The product of this polymerization has an OH number of 136, an acid number of 0.04, total unsaturation of 0.0069 meq/g, 60 ppm of water, a viscosity of 189 mPa·s at 50° C., and a density of 1.026 g/cm³ at 25° C. It contains 11.8% primary hydroxyl groups and 88.2% secondary hydroxyl groups. $M_n$ by GPC is 1030 g/mol, polydispersity is 1.11.

EXAMPLE 2

1340.5 g (2.96 mol) of the VORANOL CP450 polyol and 877.8 g (5.93 mol) phthalic anhydride are added to a reactor and flushed 10 times with nitrogen. The reactor is thermostated at 100° C. with 600 kPa of $N_2$ pressure and stirring. The reaction mixture is stirred for 16 hours. The $N_2$ pressure is reduced to 100 kPa and the temperature is increased to 130° C. Propylene oxide (678.0 g, 11.67 mol) is fed to the reactor at an average feed rate of 6.8 g/min over 100 minutes. At the completion of the feed the total pressure in the reactor has reached 490 kPa. The mixture is digested another 45 minutes at 130° C., during which time the pressure in the reactor decreases to 440 kPa.

A 273.0 g sample of the reaction mixture is removed and unreacted propylene oxide removed under vacuum. Solid DMC catalyst complex (0.422 g) is dispersed in the stripped polyol sample. The resulting dispersion contains 1545 ppm of the DMC catalyst. 54.3 g of the DMC catalyst dispersion is injected into the 130° C. reactor and stirred for 100 minutes. No DMC catalyst activation is observed.

The reactor temperature is increased to 140° C. An additional 54.7 g of the DMC catalyst dispersion is injected into the reactor, followed by a feed of additional 98 g (1.69 mol) of PO an stirring for another 30 min. No catalyst activation is observed.

An additional 94.4 g of the DMC catalyst dispersion is injected into the reactor, followed by 45 minutes more stirring. No catalyst activation is observed.

The remaining 69.2 g of the DMC catalyst dispersion is mixed with 2.25 g of aluminum isobutoxide and injected into the reactor. Smooth DMC catalyst activation, accompanied by a pressure drop in the reactor and an exotherm, is observed within 10 min following the injection. An additional 827 g (14.24 mol) of PO are fed to the reactor at 30 g/minute, followed by digesting for another 30 minutes. A colorless viscous liquid is obtained.

The product of this polymerization has an OH number of 140, an acid number of 0.09, total unsaturation of 0.0092 meq/g, 120 ppm of water, a viscosity of 687 mPa·s at 50° C., and a density of 1.097 g/cm³ at 25° C. It contains 18.5% primary hydroxyl groups and 81.5% secondary hydroxyl groups. $M_n$ by GPC is 1000 g/mol, polydispersity is 1.13.

EXAMPLE 3

1066.4 g (2.37 mol) of the VORANOL CP450 polyol and 1053.0 g (7.11 mol) phthalic anhydride are added to a reactor and flushed 10 times with 600 kPa nitrogen ($N_2$) pressure. The reactor is thermostated at 110° C. with 600 kPa of $N_2$ pressure and stirring for 16 hours. The $N_2$ pressure in the reactor is reduced to 100 kPa, temperature is increased to 130° C. and propylene oxide (825.0 g, 14.20 mol) is fed to the reactor at an average feed rate of 2.8 g/min over 290 minutes. At the completion of the feed the total pressure in the reactor has reached 490 kPa. The mixture is digested for 21 hours during which time the pressure in the reactor decreases only to 290 kPa. A 93.0 g sample is removed from the reactor and unreacted propylene oxide is stripped off.

0.111 g of DMC catalyst and 2.25 g of Al(s-BuO)$_3$ are dispersed in the stripped polyol sample. The dispersion contains 1200 ppm of the DMC catalyst. Reactor temperature is increased to 140° C. The DMC catalyst dispersion is injected into the 40° C. reactor, followed by a feed of additional 100 g (1.72 mol) of propylene oxide. Smooth DMC catalyst activation, accompanied by a pressure drop in the reactor and an exotherm, is observed within 30 minutes following the injection. An additional 150 g (2.58 mol) of propylene oxide are fed to the reactor at 30 g/minute, followed by digesting for 30 minutes. A colorless viscous liquid is obtained.

The product of this polymerization has an OH number of 129, an acid number of 1.31, total unsaturation of 0.0097 meq/g, 300 ppm of water and a viscosity of 3150 mPa·s at 50° C. It contains 20.9% primary hydroxyl groups and 71% secondary hydroxyl groups. $M_n$ by GPC is 990 g/mol, polydispersity is 1.15.

The invention claimed is:

1. A method for producing a hybrid polyester-polyether, comprising polymerizing at least one alkylene oxide in the presence of (1) a carboxylate initiator compound, (2) a double metal cyanide catalyst complex and (3) a Group 3-Group 15 metal or lanthanide series metal compound not present during the preparation of the double metal cyanide catalyst complex, in which Group 3-Group 15 metal or lanthanide series metal compound a Group 3-Group 15 metal or lanthanide series metal is bonded to at least one alkoxide, aryloxy, acyl, pyrophosphate, phosphate, thiophosphate, dithiophosphate, phosphate ester, thiophosphate ester, amide, siloxide, hydride, carbamate or hydrocarbon anion, and wherein the Group 3-Group 15 metal or lanthanide series metal compound is devoid of halide anions.

2. The method of claim 1, wherein the carboxylate initiator has at least one carboxyl (—COOH) or carboxylate (—COO⁻) group, or a carboxylate precursor group which produces a carboxyl or carboxylate group under the conditions of the polymerization.

3. The method of claim 2 wherein the carboxylate initiator is an alkanoic monoacid having from 1 to 30 carbon atoms, a keto acid, an aromatic mono- or di-acids, an aliphatic dicarboxylic acid, a tricarboxylic acid, a hydroxyacid, an unsaturated monocarboxylic acid, or an aminoacid.

4. The method of claim 2 wherein the carboxylate initiator is an anhydride of a dicarboxylic acid.

5. The method of claim 2 wherein the carboxylate initiator is a half acid ester formed in the reaction of a carboxylic acid anhydride compound with a polyol compound.

6. The method of claim 5 wherein the polyol compound is a polyester polyol, a polyether-polyester polyol, or a polyether polyol, such as ethylene glycol, diethylene glycol, propylene glycol, dipropylene glycol, 1,3-propanediol, 1,4-butanediol; 1,5-pentanediol, 1,6-hexanediol, 1,4-cyclohexanedimethanol, 1,8-octanediol; neopentyl glycol; 1-3 butanediol; 2,2,4-trimethyl-1,3-pentanediol, dimethylolpropane, glycerine, trimethylolpropane, trimethylolethane, pentaerythritol, 1,2,4-butanetriol, 1,2,6-hexanetriol, erithritol, xylitol or sorbitol.

7. The method of claim 5 wherein the half acid ester compound is formed in situ by performing the polymerization of the alkylene oxide in the presence of the carboxylic acid anhydride and polyol compounds.

8. The method of claim 2 wherein the carboxylate initiator is a half acid amide formed in the reaction of a carboxylic acid anhydride compound with ethanol methyl amine, 3-propanol methyl amine, 2-propanol methyl amine, bis-(2-hydroxypropyl)amine, triethanolamine, diethanolamine, N,N' dimethyl ethylenediamine, N,N' dimethyl butylene diamine, N,N' dimethyl toluenediamine, or N,N' dimethyl phenylenediamine.

\* \* \* \* \*